(12) United States Patent
Guo et al.

(10) Patent No.: US 7,662,412 B2
(45) Date of Patent: Feb. 16, 2010

(54) TRADITIONAL CHINESE MEDICINE COMPOSITION TO TREAT RHEUMATOID ARTHRITIS AND PREPARATION METHOD THEREOF

(76) Inventors: Laiwang Guo, Room 1406, No. 6 Building, Dayingpan Officer Residential Section, Taiyuan, Shanxi 030000 (CN); Haiming Guo, Room 1406, No. 6 Building, Dayingpan Officer Residential Section, Taiyuan, Shanxi 030000 (CN)

(*) Notice: Subject to any disclaimer, the term of this patent is extended or adjusted under 35 U.S.C. 154(b) by 127 days.

(21) Appl. No.: 11/989,002

(22) PCT Filed: Jul. 18, 2005

(86) PCT No.: PCT/CN2005/001065
§ 371 (c)(1),
(2), (4) Date: Mar. 26, 2008

(87) PCT Pub. No.: WO2007/009291
PCT Pub. Date: Jan. 25, 2007

(65) Prior Publication Data
US 2009/0148536 A1    Jun. 11, 2009

(51) Int. Cl.
*A01N 65/00* (2006.01)
(52) U.S. Cl. .................................... 424/725
(58) Field of Classification Search ........................ None
See application file for complete search history.

(56) References Cited

U.S. PATENT DOCUMENTS

2006/0110468 A1* 5/2006 Liu et al. .................... 424/725

FOREIGN PATENT DOCUMENTS

| CN | 1311013 A | 9/2001 |
| CN | 1327841 A | 12/2001 |

* cited by examiner

*Primary Examiner*—Michael V Meller
(74) *Attorney, Agent, or Firm*—Birch, Stewart, Kolasch & Birch, LLP

(57) ABSTRACT

The present invention discloses a traditional Chinese medicine composition to treat Rheumatoid Arthritis and its preparation method. The composition is mainly comprised of the following crude drugs: ant, Radix Salviae Miltiorrhizae, Radix Aconiti Preparata, Radix Ginseng, Caulis Spatholobi, and Ramulus Cinnamomi, etc. According to pharmaceutical methods, various clinical acceptable dosage forms can be prepared of the composition of the present invention, including but not limited to one of the following dosage forms: tablets, capsules, pills, granules, suspension, dripping pills, oral liquid preparation, etc. The drug of the present invention has the functions of invigorating the kidney and spleen, promoting blood flow and clearing out the vein, expelling wind-evil and removing wetness, eliminating cold to stop pain. It can be effectively used in the treatment of lingering arthralgia with weak, arthralgia, intumesce and morning stiffness, numbness and stickiness, difficult to flex and extend, rigor and deforming, the rheumatism and rheumatoid arthritis with the above symptoms.

14 Claims, No Drawings

TRADITIONAL CHINESE MEDICINE COMPOSITION TO TREAT RHEUMATOID ARTHRITIS AND PREPARATION METHOD THEREOF

FIELD OF THE INVENTION

The present invention relates to a traditional Chinese medicine composition and preparation method thereof. In particular, it relates to a traditional Chinese medicine composition to treat rheumatoid arthritis and preparation method thereof, and belongs to the field of medical art.

BACKGROUND OF THE INVENTION

Rheumatism is a common and frequently encountered disease, and has a long onset period and various clinic appearances. It is refractory disease which needs a long period of therapy. It is difficult to diagnose, cure and research this kind of pathological change due to various reasons, such as the complicated cause and pathogenesis of the disease, the borderline and multidisciplinary appearance in clinic, and additionally the limitation of the science of Traditional Chinese Medicine and the divided cognition of this disease etc. In the science of Traditional Chinese Medicine, rheumatism is collectively called "Paralysis Syndrome". It is recorded in Article 43 of Paralysis Syndrome Section of "Huangdi Neijing Suwen" that the three evils, wind, cold and wet, combine and cause appearance of paralysis syndrome. Domination of wind causes peripatetic paralysis, domination of cold causes pain paralysis, and domination of wet cause sticky paralysis. The therapeutic principal of this symptom is to eliminate wind, remove wet, warm meridian, and expel cold to expel these three kinds of pathogens to cure the disease.

SUMMARY OF THE INVENTION

One of the purposes of the present invention is to provide a traditional Chinese medicine composition to treat rheumatoid arthritis; another purpose is to provide a method of preparing this composition.

The present invention can be implemented through the following three technical schemes:

Scheme 1: the Constitutes and Formula of Crude Drugs for the Traditional Chinese Medicine Composition are as Follows (According to Weight Ratio):

| | |
|---|---|
| Ant | 280-500 parts |
| Radix Salviae Miltiorrhizae | 100-200 parts |
| Radix Aconiti Preparata | 35-100 parts |
| Radix Ginseng | 20-80 parts |
| Caulis Spatholobi | 30-75 parts |
| Ramulus Cinnamomi | 25-80 parts; |

Wherein scheme 1, the constitutes and formula of crude drugs for traditional Chinese medicine composition are preferably as follows:

| | |
|---|---|
| Ant | 300-400 parts |
| Radix Salviae Miltiorrhizae | 120-150 parts |
| Radix Aconiti Preparata | 40-70 parts |
| Radix Ginseng | 30-50 parts |
| Caulis Spatholobi | 40-60 parts |
| Ramulus Cinnamomi | 35-50 parts. |

Scheme 2: the Constitutes and Formula of Crude Drugs for the Traditional Chinese Medicine Composition are as Follows (According to Weight Ratio):

| | |
|---|---|
| Ant | 280-500 parts |
| Radix Salviae Miltiorrhizae | 100-200 parts |
| Radix Aconiti Preparata | 35-100 parts |
| Radix Ginseng | 20-80 parts |
| Caulis Spatholobi | 30-75 parts |
| Ramulus Cinnamomi | 25-80 parts |
| Cortex Kalopanacis | 25-70 parts |
| Herba speranskiae tuberculatae | 25-70 parts |
| Cortex Phellodendri | 25-70 parts |
| Rhizoma Atractylodis | 25-70 parts |
| Rhizoma Alismatis | 25-70 parts |
| Herba Lycopodii | 25-70 parts |
| Semen Coicis | 35-70 parts; |

Wherein scheme 2, the constitutes and formula of crude drugs for traditional Chinese medicine composition are preferably as follows:

| | |
|---|---|
| Ant | 300-400 parts |
| Radix Salviae Miltiorrhizae | 120-150 parts |
| Radix Aconiti Preparata | 40-70 parts |
| Radix Ginseng | 30-50 parts |
| Caulis Spatholobi | 40-60 parts |
| Ramulus Cinnamomi | 35-50 parts |
| Cortex Kalopanacis | 35-50 parts |
| Herba speranskiae tuberculatae | 35-50 parts |
| Cortex Phellodendri | 35-50 parts |
| Rhizoma Atractylodis | 35-50 parts |
| Rhizoma Alismatis | 35-50 parts |
| Herba Lycopodii | 35-50 parts |
| Semen Coicis | 45-70 parts. |

Scheme 3: the Constitutes and Formula of Crude Drugs for the Traditional Chinese Medicine Composition as Follows (According to Weight Ratio):

| | |
|---|---|
| Ant | 280-500 parts |
| Radix Salviae Miltiorrhizae | 100-150 parts |
| Radix Aconiti Preparata | 35-70 parts |
| Radix Ginseng | 20-50 parts |
| Caulis Spatholobi | 30-75 parts |
| Semen Coicis | 35-70 parts |
| Cortex Kalopanacis | 25-70 parts |
| Herba speranskiae tuberculatae | 25-70 parts |
| Cortex Phellodendri | 25-50 parts |
| Rhizoma Atractylodis | 25-50 parts |
| Rhizoma Alismatis | 25-50 parts |
| Herba Lycopodii | 25-50 parts |
| Ramulus Cinnamomi | 25-50 parts |
| Scolopendra | 4-10 parts |
| Zaocys | 4-10 parts; |

Wherein scheme 3, the composition constitutes and formula of crude drugs for traditional Chinese medicine are preferably as follows:

| | |
|---|---|
| Ant | 300-400 parts |
| *Radix Salviae Miltiorrhizae* | 120-140 parts |
| *Radix Aconiti Preparata* | 45-60 parts |
| *Radix Ginseng* | 20-50 parts |
| *Caulis Spatholobi* | 45-60 parts |
| *Semen Coicis* | 45-60 parts |
| *Cortex Kalopanacis* | 35-60 parts |
| *Herba speranskiae tuberculatae* | 35-60 parts |
| *Cortex Phellodendri* | 25-40 parts |
| *Rhizoma Atractylodis* | 25-40 parts |
| *Rhizoma Alismatis* | 25-40 parts |
| *Herba Lycopodii* | 25-40 parts |
| *Ramulus Cinnamomi* | 25-40 parts |
| *Scolopendra* | 4-10 parts |
| *Zaocys* | 4-10 parts. |

According to pharmaceutical methods, various clinical acceptable dosage forms can be prepared by the medical composition of the present invention, including but not limited to one of the following forms: tablets, capsules, pills, granules, suspension, dripping pills, and oral liquid preparation, etc.

In each technical scheme of the present invention, the manufacturing process of capsule of each traditional Chinese medicine composition is as follows:

Pulverize crude drugs: ant, Radix Ginseng, Radix Aconiti Preparata, and/or Scolopendra, Zaocys to fine powder, sieve and mix well; pulverize Radix Salviae Miltiorrhizae, Ramulus Cinnamomi and/or Rhizoma Atractylodis to coarse powder respectively, percolate with 70-90% alcohol as solvent, pressure reduction concentrate the percolate by recovering alcohol to obtain the extract with relative density of 1.30-1.32 (55° C.). Combine the residues with Caulis Spatholobi, and/or Semen Coicis, Cortex Kalopanacis, Herba speranskiae tuberculatae, Cortex Phellodendri, Rhizoma Alismatis, Herba Lycopodii and decoct with water for two times, 1.5 hours each time, combine all the decoction, filter, pressure reduction concentrate the filtrates to obtain the extract with relative density of 1.35-1.38 (60° C.), add the above fine powder and the extracts of Radix Salviae Miltiorrhizae and the others, mix well, make granules, dry, crush, sieve, and fill into the capsules for use.

In each technical scheme of the present invention, the manufacturing process of dripping pills of each traditional Chinese medicine composition is as follows:

Pulverize the crude drugs: ant, Radix Ginseng, Radix Aconiti Preparata, and/or Scolopendra, Zaocys to fine powder, sieve and mix well; pulverize Radix Salviae Miltiorrhizae, Ramulus Cinnamomi and/or Rhizoma Atractylodis to coarse powder respectively, percolate with 70-90% alcohol as solvent, pressure reduction concentrate the percolate by recovering alcohol to obtain the extract with relative density of 1.30-1.32 (55° C.). Combine the residues with Caulis Spatholobi, and/or Semen Coicis, Cortex Kalopanacis, Herba speranskiae tuberculatae, Cortex Phellodendri, Rhizoma Alismatis, Herba Lycopodii and decoct with water for two times, 1.5 hours each time, combine all the decoction, filter, pressure reduction concentrate the filtrates to obtain the extract with relative density of 1.35-1.38 (60° C.), add the above fine powder and the extracts of Radix Salviae Miltiorrhizae and the others, mix well, make granules, add the above granules in PEG molten by hexane, stir well, transfer the mixture to the feeding container of dropping machine, keep the temperature at 90° C. and drop into methyl silicone oil cooled until 5~10° C. at the speed of 30 r/min, take out the dripping pills and remove the coolant by absorption, and dry for use.

In each technical scheme of the present invention, all the traditional Chinese medicine compositions have the function of invigorating the kidney and spleen, promoting blood flow and clearing out the vein, expelling wind-evil and removing wetness, eliminating cold to stop pain. It can be effectively used in the treatment of lingering arthralgia with weak, arthralgia, intumesce and morning stiffness, numbness and stickiness, difficult to flex and extend, rigor and deforming, the rheumatism and rheumatoid arthritis with above symptoms.

The prescription composition of the present invention is reasonable and the manufacturing process is advanced, which meets the needs of thinking and method in developing modern traditional Chinese medicine and establish a new way to the scientific research of traditional Chinese medicine.

Compared with pills, the capsule of the present invention has the following superiorities: smaller dosage, quick dissolubility in intestine and stomach, complete absorption, operate quickly, convenient to take and so on.

Various animal models of inflammation and pain were established, and rats and mice were orally administrated with the capsule of the present invention with dose of 0.75-3 g/kg (correspond to 7.5-30 times as human's daily dosage), and demonstrated that the said capsule has the anti-inflammatory and analgesic effects. The said capsule can obviously relieve the primary and the secondary affection of voix pedis swelling and adjuvant-induced arthritis of rats induced by egg albumen and methanal. It can inhibit the capillary permeability of mouse's abdominal cavity in the early stage, and can inhibit the transmigration of leukocyte under the rat's skin, and also can inhibit the forming of granuloma induced by cotton ball in the later stage of inflammation. It can relieve the mouse's pain induced by hot plate stimulus and acetic acid's writhing response. It can inhibit LPS induced AA rat's PM and can release IL-1; indirect luminescence immunoassay indicates that this drug can increase the quantity of Ts cells, and the ratio of $L^3T^+_4/Lyt-2^+$ cells was obviously lower than control group.

The etiopathogenesis, diseased region and peculiarity of rat's adjuvant-induced arthritis are similar to human's rheumatoid arthritis. The primarily pathological changes of the voix pedis injected with adjuvant belongs to a non-specific inflammation, and the secondary pathological changes of the voix pedis injected no adjuvant belongs to immunoreactive inflammation. The said capsule can inhibit rat AIA, which indicate that it has effect of inhibiting rheumatoid arthritis. It has effect of inhibiting swelling induced by egg albumen and methanal, it can inhibit increasing capillary permeability of mouse's abdominal cavity induced by acetic acid and can inhibit the transmigration of leukocyte under the rat's skin induced by CMC. All above indicate that the said capsule has releasing effect in the early stage of inflammation. It can inhibit the forming of granulomatous induced by cotton ball indicates it has anti-inflammatory effect in the multiplication period of inflammation. In the experiments of the mouse's pain induced by hot plate stimulus and acetic acid's writhing response, the capsule can prolong eclipse period and decrease the number of times, which indicate that it can elevate the tolerance to the pain and more or less has some analgesic effect.

The present invention is described further through the following experiments and examples.

EXPERIMENT 1

Anti-Inflammatory Action of the Present Invention

1. Effect on Voix Pedis Swelling of Rat Induced by Egg Albumen 50 rats with body weight of 180-200 g were randomly divided into 5 groups: high, middle, low dosage of the capsule, Tripterygii Wilfordii group and control, 10 rats each group, gaster-poured once a day for 7 days continuously. One hour after the last intragastric infusion, subcutaneous inject 0.1 ml of 10% fresh egg albumen with NS in the middle of each rat's right post voix pedis, then measure the thickness of voix pedis using vernier caliper at 15 min, 30 min and 4 hours before and after injection. The position and closeness in each measurement were the same. The difference of thickness before injection and after injection was the swelling degree in different time. The results were showed in Table 1, compared with control, except for no obvious change in 15 min for low dosage, all the other groups had the obvious effect of releasing swelling within 4 hours. Moreover, the effect was correlated to the dosage.

TABLE 1

Effect on Voix Pedis Swelling of Rats induced by Egg Albumen

| Groups | Dosage (g/kg) | Number of rat | Degree of swelling (mm, $\overline{X} \pm S$) | | |
|---|---|---|---|---|---|
| | | | 15 min | 30 min | 4 h |
| Control | | 10 | 1.7 ± 0.2 | 2.1 ± 0.4 | 1.6 ± 0.2 |
| The said capsule group | 3 | 10 | 1.0 ± 0.2*** | 1.5 ± 0.3*** | 1.0 ± 0.2*** |
| The said capsule group | 1.5 | 10 | 1.3 ± 0.2*** | 1.7 ± 0.2** | 1.2 ± 0.2*** |
| The said capsule group | 0.75 | 10 | 1.4 ± 0.4* | 1.7 ± 0.3** | 1.3 ± 0.2*** |
| Tripterygii Wilfordii group | triptolide 66 μg | 10 | 1.0 ± 0.2*** | 1.2 ± 0.4*** | 1.0 ± 0.2*** |

Compared with control:
***P < 0.01
**P < 0.05
*P > 0.05

2. Effect on Voix Pedis Swelling of Rat Induced by Methanal 50 rats, with same body weight and the groups as Experiment 1 were gaster-poured 1 time each day for 10 days. The thickness of voix pedis on the 7$^{th}$ day was measured by vernier caliper. Then subcutaneous inject 0.1 ml of 2.5% methanal in the middle of each rat's right post voix pedis, measure the thickness of voix pedis at 12 h, 24, and 72 h after injection. The difference of thickness between before injection and after injection was the swelling degree in different time. The results were shown in Table 2: compared with control, all the residue groups had the obvious effect of releasing swelling from 12 to 72 hours. The difference is significance in statistics. Moreover, the effect was correlated to the dosage.

3. Effect on Rat's AIA 40 male rats with body weight of 170-190 g were randomly divided into 5 groups: high, middle, low dosage of the capsule, Tripterygii Wilfordii group and control, 8 rats each group. Subcutaneous inject 0.05 ml Freund's complete adjuvant (FCA) in the middle of each rat's left behind voix pedis to cause inflammation, (the preparation methods of FCA: liquid paraffin with Lanolin (2:1), heat them to 70° C. and mix well, autoclaving; then and 7.5 mg Bacillus Calmette-Guerin Vaccine per 1 ml). 6 days after the forming of the inflammation, gaster-poured 1 time each day for 20 days. Measure the volume of both posterior part voix pedis. The difference between posterior part and anterior part in the same side was the swelling degree. Meanwhile measure the body weight, and observe the change. The results were shown in Table 3, 4, and 5.

TABLE 2

Effect on Voix Pedis Swelling of Rats Induced by Methanal

| Groups | Dosage (g/kg) | Number of rat | Degree of swelling (mm, $\overline{X} \pm S$) | | |
|---|---|---|---|---|---|
| | | | 12 h | 24 h | 72 h |
| Control | | 10 | 2.1 ± 0.4 | 2.1 ± 0.4 | 2.3 ± 0.4 |
| The said capsule group | 3 | 10 | 1.3 ± 0.3*** | 1.6 ± 0.2*** | 1.4 ± 0.3*** |
| The said capsule group | 1.5 | 10 | 1.6 ± 0.3*** | 1.8 ± 0.2*** | 1.7 ± 0.3*** |
| The said capsule group | 0.75 | 10 | 1.7 ± 0.3** | 2.0 ± 0.3*** | 1.8 ± 0.3*** |
| Tripterygii Wilfordii group | triptolide 66 μg | 10 | 1.3 ± 0.3*** | 1.6 ± 0.2*** | 1.4 ± 0.3*** |

Compared with control:
***P < 0.01
**P < 0.05

TABLE 3

Effect on the Primary Affection of Rat's AIA

| Group | Dosage (g/kg) | Number of rat | Swelling degree of left pedes after inject adjuvant (mL) | | | |
|---|---|---|---|---|---|---|
| | | | 8 日 | 13 日 | 18 日 | 23 日 |
| Control group | | 8 | 0.34 ± 0.06 | 0.41 ± 0.05 | 0.42 ± 0.05 | 0.34 ± 0.05 |
| The said capsule group | 1.5 | 8 | 0.30 ± 0.06* | 0.33 ± 0.06** | 0.33 ± 0.04*** | 0.29 ± 0.04** |
| The said capsule group | 0.75 | 8 | 0.32 ± 0.05* | 0.37 ± 0.05* | 0.37 ± 0.04** | 0.32 ± 0.03* |
| Tripterygii Wilfordii group | triptolide 66 μg | 8 | 0.28 ± 0.04** | 0.31 ± 0.05*** | 0.31 ± 0.05*** | 0.27 ± 0.05** |

Compared with control:
*P > 0.05
**P < 0.05
***P < 0.01

TABLE 4

Effect on the secondary affection of rat's AIA

| Group | Dosage (g/kg) | Number of rat | Swelling degree of left pedes after inject adjuvant (mL) | | |
|---|---|---|---|---|---|
| | | | 15 d | 20 d | 25 d |
| Control group | | 8 | 0.24 ± 0.06 | 0.26 ± 0.07 | 0.21 ± 0.05 |
| The said capsule group | 3 | 8 | 0.15 ± 0.04*** | 0.14 ± 0.04*** | 0.12 ± 0.03*** |
| The said capsule group | | 8 | 0.17 ± 0.04** | 0.18 ± 0.06** | 0.15 ± 0.03*** |
| The said capsule group | 0.75 | 8 | 0.20 ± 0.03* | 0.20 ± 0.03** | 0.17 ± 0.04* |
| Tripterygii Wilfordii group | triptolide 66 μg | 8 | 0.15 ± 0.03*** | 0.15 ± 0.03*** | 0.12 ± 0.02*** |

Compared with control:
*P > 0.05
**P < 0.05
***P < 0.01

TABLE 5

Effect on the body weight of rat's AIA

| Group | Dosage (g/kg) | Number of rat | The body weight after inject adjuvant(mL) (g, $\overline{X} \pm S$) | | |
|---|---|---|---|---|---|
| | | | 0 d | 15 d | 25 d |
| Control group | | 8 | 184 ± 7 | 190 ± 8 | 194 ± 9 |
| The said capsule group | 3 | 8 | 183 ± 7 | 199 ± 9 | 209 ± 9*** |
| The said capsule group | 1.5 | 8 | 186 ± 6 | 198 ± 9 | 207 ± 9** |
| The said capsule group | 0.75 | 8 | 185 ± 7 | 195 ± 7 | 202 ± 7 |
| Tripterygii Wilfordii group | triptolide 66 μg | 8 | 185 ± 7 | 200 ± 7** | 208 ± 7*** |

Compared with control:
**P < 0.05
***P < 0.01

The above results indicated that the primary affection of swelling was the most obvious at half a month after inject adjuvant, and it of the capsule group was relieved obviously. The opposite side of pedes and the joint of forward pedes were swelling with no injection, namely the secondary affection of immunoreactive inflammation. This kind of inflammation was also obviously relieved in capsule group with high, middle and low dosage. The rats in control group ate less, and their body weigh was decreased. Compared with capsule group, the significance difference between the control and the capsule was obvious at the 25$^{th}$ day.

4. Effect on Capillary Permeability of Mouse's Abdominal Cavity 50 white mice, with body weight of 20-24 g, half female and half male, were randomly divided into four groups: high, center, and the low dosage (lavage) of the said capsule, Hydrocortisone (i.m) group and control group. The mouse were administered once a day for 5 days, inject intravenously 0.1 ml/10 g of 0.5% azovan blue isotonic Na chloride into each mouse tail after 1 hour of the last administration, then intraperitoneal inject with 0.2 ml of 0.6% glacial acetic acid physiological saline to each. Then execute them on cervical vertebra after 20 minutes, cut the belly open, flush the abdominal cavity with 6 ml of the physiological saline for several times, collect the eluates, add isotonic Na chloride to 10 ml, centrifuge at 3000 rpm for 15 minutes, measure the absorbability of supernatant at wave length of 590 nm. The results were shown in Table 6. When the abdominal cavity inflammation was induced by acetic acid and capillary permeability was increased, the effusion of influxed staining solution and the capillary permeability were reduced by the use of the said capsule, which demonstrated the said capsule had the anti-inflammation function. The difference between high dose group and control group was obvious statistically.

6. Effect on the Formation of Granuloma of Rat's Tampon 50 rats with body weight of 168±11 g were randomly divided into six groups: high, middle, and the low dosage of the said capsule, Tripterygium Wilfordii group and control group, 10 rats each group. Incise on median line of the lower abdomen, embed 20 mg of autoclaved cotton ball into left and right subcutaneous groin respectively using tweezers for eyes. Gaster-poured on that day, once a day for 7 days. Execute the rats and strip the tampon wrapped with granulation tissue, and place it in baking oven at temperature of 50° C., weigh after 1.2 hours, the resultant weight minus the

TABLE 6

Effect on the Increase of Capillary Permeability of Rat Abdominal Cavity

| Group | Dosage (g/kg) | Route of administration | Number of rat | Absorbability of colorant from abdominal cavity $\overline{X} \pm S$ | Inhibition ratio (%) | P |
|---|---|---|---|---|---|---|
| Control group | | | 10 | 0.172 ± 0.091 | | |
| The said capsule group | 3 | ig | 8 | 0.101 ± 0.021 | 41.3 | <0.05 |
| The said capsule group | 1.5 | ig | 7 | 0.116 ± 0.064 | 32.6 | >0.05 |
| The said capsule group | 0.75 | ig | 9 | 0.110 ± 0.023 | 36.0 | >0.05 |
| Hydrocortisone group | 0.02 | im | 7 | 0.153 ± 0.054 | 11.0 | >0.05 |

5 Effect on Leukoplania in Carboxymethyl Cellulose of Rat 24 rats with body weight of 300±60 g, half female and half male, were randomly divided into 4 groups of high, low dosage of the said capsule, Radix Tripterygii Wilfordii Tablets group and control group, 6 rats each group. Gaster-poured once a day for 3 days continuously. On second day of administration, cut and sterilize every rat's capill on the nape, hypodermoclysis infuse with 5 ml of air. On the next day, infuse 5 ml of 1.5% carboxymethyl cellulose (CMC) physiological saline into air sac for inflammation, draw-off 0.1 ml of CMC liquid from air sac after 3 and 7.5 hours respectively, influx it into 3 ml of brilliant cresyl blue staining solution, mix well and stain, count the number of leucocytes under microscope. The results were shown in Table 7. As a bland pro-inflammatory agent, CMC was injected into rat subcutaneously, inducing aggregation of leucocyte partly, increasing lencocyte count of displacing liquid. The count of control group was higher than normal general one, whereas each administration group was decreased, which indicates that the acute inflammatory was inhibited. As a result of the larger error method, only a low dose of three hours of lower value compared with control group had statistically significant differences.

TABLE 7

Effect on Euko (cyto) Plania in Subcutaneous CMC of Rat

| Group | Dosage (g/kg) | Number of rat | Number of leucocyte in CMC (10⁹/L) | |
|---|---|---|---|---|
| | | | 3 hours | 7.5 hours |
| Control group | | 6 | 11.4 ± 5.6 | 18.8 ± 9.0 |
| The said capsule group | 4 | 6 | 8.7 ± 1.9 | 12.8 ± 7.5 |
| The said capsule group | 2 | 6 | 5.6 ± 2.1** | 12.2 ± 3.3 |
| Tripterygium Wilfordii group | triptolide 66 μg | 6 | 7.8 ± 2.0 | 13.3 ± 2.8 | weight of cotton ball was thus net weight of granuloma. The results were shown in Table 8. The subjects of high, medium dose can significantly reduce the weight of granuloma that inhibit desmoplasia of chronic inflammation.

TABLE 8

Effect on the formation of granuloma of rat's tampon

| Group | Dosage (g/kg) | Number of rat | Granuloma (mg) | P |
|---|---|---|---|---|
| Control group | | 10 | 99.8 ± 16.5 | |
| The said capsule group | 3 | 10 | 81.0 ± 5.4 | <0.01 |
| The said capsule group | 1.5 | 10 | 84.5 ± 5.3 | <0.05 |
| The said capsule group | 0.75 | 10 | 98.3 ± 16.1 | >0.05 |
| Tripterygium Wilfordii group | triptolide 66 μg | 10 | 82.2 ± 11.0 | <0.05 |

EXAMPLE 2

The Said Capsule's Analgesic Effect

1. Hot Plate Method

Provide female mouse (unpregnancy) with body weight of 18 to 22 grams, and put them on the metal plate of thermostatic waterbath at a temperature of 55±0.5° C. respectively. Record the reaction time between the time the mouse was put on the hot plate to the time they lick their metalegs using electric 1/100 stop watch. Choose 50 mouse whose reaction time range from 10-30 seconds, and randomized them into 5 groups: the high, middle and low dosage of the said capsule group respectively, the Tripterygium Wilfordii group and control group, with 10 mouse in each group. Gaster-poured once a day for 7 days continuously. After one hour after the last administration, record the hot plate reaction time as the method mentioned above, and count the extended rate of reaction time and significance of difference of each administration group compared with control group. The result had been shown at Table 9. Each dosages of the said capsule can significantly prolong the reaction time of heat stimulation, and increase threshold of pain.

TABLE 9

Effect on reaction times by hot plate method to mouse

| Group | Dosage (g/kg) | Numbers of mouse | RT (s) | Change rate (%) | P |
|---|---|---|---|---|---|
| Control group | | 10 | 22.1 ± 5.8 | 100 | <0.01 |
| The said capsule group | 3 | 10 | 64.1 ± 7.9 | 290 | <0.01 |
| The said capsule group | 1.5 | 10 | 46.5 ± 8.2 | 210 | <0.01 |
| The said capsule group | 0.75 | 10 | 38.6 ± 6.8 | 175 | <0.01 |
| *Tripterygium Wilfordii* group | triptolide 66 μg | 10 | 65.8 ± 7.5 | 298 | <0.01 |

2. Writhing Method to Mouse 50 mouse were randomly divided into 5 groups, 10 mouse each group, and half male and half female. Gaster-poured once a day for 7 days continuously. After one hour after the last administration, inject each mouse (i.p.) 0.1 ml/10 g of 0.6% acetic solution, and observe each one's reactive writhing times immediately in 20 minutes. Count reactive inhibition ratio and significance of difference of each administration group compared with control group. As can be seen from Table 10, the said capsule can reduce over 50% of the pain induced by injecting acetic solution, and the difference was of highly significance.

TABLE 10

Effect on writhing response to mouse injected with acetic acid

| Group | Dosage (g/kg) | Numbers of mouse | Writhing times ($\bar{X}$ ± SD) | Inhibition ratio (%) | P |
|---|---|---|---|---|---|
| Control group | | 10 | 48.4 ± 8.8 | | |
| The said capsule group | 3 | 10 | 11.3 ± 4.5 | 76.6 | <0.01 |
| The said capsule group | 1.5 | 10 | 18.1 ± 6.7 | 62.6 | <0.01 |
| The said capsule group | 0.75 | 10 | 22.7 ± 7.6 | 53.1 | <0.01 |
| *Tripterygium wilfordii* group | triptolide 66 μg | 10 | 10.6 ± 4.5 | 78.1 | <0.01 |

EXAMPLE 3

The Said Capsule's Function of Immunological Regulation

1. Effect on interleukin-1 (IL-1) Activity of the Rat with Adjuvant-Induced Arthritis Fizzer complete adjuvant (from Sigma Co.) was emulsified and injected subcutaneously and sterilely 0.1 ml into the right meta voix pedis of each rat (♂, 160±20 g) to establish a model of adjuvant-induced arthritis.

Preparation of peritoneal macrophage: Execute rats at $25^{th}$ days after injecting complete adjuvant, then rapidly inject proper amount of Hank's solution into the belly of them, and rub their abdominal wall several times before collecting peritoneal fluid. Wash it with Hank's solution containing 5% calf serum twice, then prepare $1 \times 10^6$/mL cell suspension with wholly swelling RPMI1640. Transfer into a culture plate with 24 wells, 1 ml each well. Incubate them in a 5% $CO_2$ incubator overnight at a temperature of 37° C., abandon the supernatant fluid, wash with pre-warmed Hank's solution containing 5% calf serum at 37° C. twice, and remove un-adherent cell. The residue was peritoneal macrophage.

2. IL-1 induction: Add 10 μg/mL lipopolysaccharide (LPS) to the above culture plate with 24 wells, then incubate for 24 hours, centrifuge (2000 rpm, 5 min), collect the peritoneal fluid, and filter with micropore filter. This solution was the IL-1 sample to be detected.

3. Measurement of IL-1 bioactivity: Take 2-3 months Balb/c mouse's thymus at sterile condition, put it into flat plate containing Hank's solution, levigate through 100 mesh grit, filter with nylon net till it becomes unicell suspension, wash twice with Hank's solution, and centrifugal method (1500 rpm. 5 min). Prepare mixed solution with ConA (2 μg/mL) and thymocyte ($1.5 \times 10^7$/mL) with wholly swelling RPMI solution. Add 100 μl of the above mixed solution and 100 μl of the IL-1 sample to each well of culture plate with 96 wells, then incubate them for 72 hours in incubator containing 5% $CO_2$, add 10 μl of 5 mg/mL NTT to each well at 4 hours before termination, dissolve formazan granules with 150 μL of acidic isopropanol (contain 0.04 mol/L HCl) after 4 hours. Determine OD value by ELIASA on the wavelength of 570 nm within 30 minutes. The results were shown in Table 11.

TABLE 11

Effect on IL-1 activity of AA rats

| Group | Dosage (g/kg) | Number of rats | OD Value |
|---|---|---|---|
| Control group | | 6 | 0.24 ± 0.01*** |
| Model group | | 6 | 0.87 ± 0.03 |
| The said capsule group | 5 | 6 | 0.48 ± 0.03*** |
| The said capsule group | 2.5 | 6 | 0.54 ± 0.01*** |
| Prednisone group | 5 mg | 6 | 0.34 ± 0.02*** |

Compared with model group: ***P < 0.01

The result indicates that LPS induce AA rat's $PM_\phi$ and releases IL-1 obviously above the normal level. The said capsule's function of inhibiting LPS and inducing rats release IL-1 indicates that it can inhibit or adjust AA rat's $PM_\phi$ releasing IL-1 exorbitantly.

2. Effect on Mouse's DTH T Cell Subsets

36 Ba11b/c mice were randomly divided into 6 groups: control group, model group, said capsule high dosage group, said capsule middle dosage group, said capsule low dosage group and prednisone group, 6 mice each group. Smear barium sulfide suspension on the belly of 5 groups of mice to depilate, except the control group. Smear 25 μl of 1% DNFB on each mouse's belly to cause sensitization the next day. On the second day smear again to strengthen the function. On the fifth day, smear 10 μl of identical concentration of DNFB on each mouse's right ear, and execute the mouse 24 hours later, then take the splenic lymphocyte and carry out the detection of T cell subsets.

Methods: Dilute rat anti-mouse $L_3T_4$ and Lyt-2 monoclonal antibody with 0.1 NPBS by the ratio of 1:10 and FITC-rabbit anti-rat IgG monoclonal antibody with 0.1 MPBS by the ratio of 1:10. Imbibe 50 μl of cultured splenic lymphocyte ($2\times10^6$ Unit/mL) induced by ConA (2 μg/mL) and transfer to V-type plate with 96 wells, centrifuge (1700 rpm, 5 min), abandon supernatant fluid, add 40 μl of anti-$L_3T_4$ or Lyt-2 monoclonal antibody and mix with 40 μl of RPMI1640 solution for non-specific stain as control. React in refrigerator at 4° C. for 30 minutes. Add 100 μl of Hank's solution to each well and centrifuge (1700 rpm, 5 min) for 3 times, abandon supernatant fluid, then add 40 μl of FITC-rabbit anti-rat IgG and mix them up, react for 30 minutes in 4° C. refrigerator. Add 100 μL of Hank's solution in each well, and centrifuge (1700 rpm, 5 min), repeat for 3 times, abandon supernatant fluid. Add 10 μL of Hank's solution in each well and mix well. Take 10 μl of the above solution on a blood counting chamber and count the number under fluorescence microscope (excitation light at 490 nm, barrier filter plate's transmission range from 520 to 530 nm). Count 200 cells of each sample and observe the number of masc-fluorescyte cells in the above 200 cells. The number of masc-fluorescyte cells subtracting the number of non-specific stain masc-fluorescyte cells equals to the number of $L_3T_4$ or Lyt-2 masc-fluorescyte cells. As is shown in Table 12, the said capsule group of high dosage had the trend of increasing yt-$2^+$ and decreasing the ratio of $L_3T_4$ ($P<0.05$).

TABLE 12

Effect on DTH T cell subsets of mouse

| Group | Dosage (g/kg) | Numbers of mouse | Cells number (%) | | $L_3T_4^+/Lyt-2^+$ |
|---|---|---|---|---|---|
| | | | $L_3T_4^+$ | Lyt-$2^+$ | |
| Control group | | 6 | 54.1 ± 1.9 | 45.6 ± 2.7 | 1.19 ± 0.07*** |
| Model group | | 6 | 64.9 ± 4.6 | 40.3 ± 2.1 | 1.56 ± 0.10 |
| The said capsule group | 5 | 6 | 62.7 ± 3.7 | 47.7 ± 5.4 | 1.34 ± 0.28** |
| The said capsule group | 2.5 | 6 | 67.5 ± 4.2 | 45.4 ± 3.0 | 1.49 ± 0.14 |
| The said capsule group | 1.25 | 6 | 69.7 ± 3.7 | 40.0 ± 2.5 | 1.53 ± 0.10 |
| Prednisone group | 5 mg | 6 | 59.6 ± 7.5 | 56.2 ± 3.8*** | 1.21 ± 0.14*** |

Compared with control:
**P < 0.05,
***P < 0.01

The dosage of the said capsule for human use was 2 g each time, 3 times per day, and the total amount was 6 g a day; the average dosage a day for adult (calculated by 60 kg) was 0.1 g/kg. Tripterygium Wilfordii Tablet was used as control drug, its dosage was 2 tablets each time, 3 times per day, and the total amount was 6 tablets per day which corresponds to 198 μg of triptolide, and the average dosage a day was 3.3 μg/kg by weight. The multiple of animal dosage to human dosage was converted by the above cardinal number.

The following examples have the same effect as the above experiments.

EXAMPLE 1

Capsule

| | |
|---|---|
| Ant | 330 g |
| Radix Salviae Miltiorrhizae | 120 g |
| Radix Aconiti Preparata | 60 g |
| Radix Ginseng | 40 g |
| Caulis Spatholobi | 60 g |
| Ramulus Cinnamomi | 40 g |
| Semen Coicis | 60 g |
| Cortex Kalopanacis | 60 g |
| Herba speranskiae tuberculatae | 60 g |
| Cortex Phellodendri | 40 g |
| Rhizoma Atractylodis | 40 g |
| Rhizoma Alismatis | 40 g |
| Herba Lycopodii | 40 g |
| Scolopendra | 5 g |
| Zaocys | 5 g |

1000 capsules were prepared according to normal manufacturing process. 0.5 g each capsule, 3 times per day, 4 capsules each time.

EXAMPLE 2

Capsule

| | |
|---|---|
| Ant | 400 g |
| Radix Salviae Miltiorrhizae | 130 g |
| Radix Aconiti Preparata | 65 g |
| Radix Ginseng | 50 g |

-continued

| | |
|---|---|
| Caulis Spatholobi | 50 g |
| Ramulus Cinnamomi | 30 g |
| Semen Coicis | 50 g |

-continued

| | |
|---|---|
| Cortex Kalopanacis | 50 g |
| Herba speranskiae tuberculatae | 50 g |
| Cortex Phellodendri | 30 g |
| Rhizoma Atractylodis | 45 g |
| Rhizoma Alismatis | 30 g |
| Herba Lycopodii | 30 g |
| Scolopendra | 8 g |
| Zaocys | 8 g |

Pulverize ant, Radix Ginseng, Radix Aconiti Preparata, Scolopendra, Zaocys into fine powder, sieve and mix it; pulverize Radix Salviae Miltiorrhizae, Ramulus Cinnamomi, Rhizoma Atractylodis into coarse power respectively, percolate with 90% alcohol as solvent, evaporate alcohol from percolate, pressure reduction concentrate the percolate by recovering alcohol to obtain the extract with relative density of 1.30-1.32 (55° C.). Combine the residues with Caulis Spatholobi, Semen Coicis, Cortex Kalopanacis, herba speranskiae tuberculatae, Cortex Phellodendri chinensis, Rhizoma Alismatis and Herba Lycopodii with water to decoct twice, 1.5 hours each time. Combine all the decoctions, filter, pressure reduction concentrate the filtrates to obtain the extract with relative density of 1.35-1.38 (60° C.). Mix the above fine power and each of extracts, mix well and make granules, dry, crush, sieve and fill in capsule for use. Fill in capsule, and each capsule contains 0.5 g. Usage: take orally, with 4 capsules per time, 3 times per day.

EXAMPLE 3

Oral Liquid

| | |
|---|---|
| Ant | 330 g |
| Radix Salviae Miltiorrhizae | 120 g |
| Radix Aconiti Preparata | 60 g |
| Radix Ginseng | 40 g |
| Caulis Spatholobi | 60 g |
| Ramulus Cinnamomi | 40 g |

In above six crude drugs, pulverize ant, Radix Ginseng, Radix Aconiti Preparata into fine powder, sieve and mix well; pulverize Radix Salviae Miltiorrhizae, Ramulus Cinnamomi into coarse power respectively, percolate with 90% alcohol as solvent, pressure reduction concentrate the percolate by recovering alcohol to obtain the extract with relative density of 1.30-1.32 (55° C.). Combine the residues with Caulis Spatholobi and decoct with water, filter, pressure reduction concentrate the filtrates to obtain the extract with relative density of 1.35-1.38 (60° C.). Mix the above fine power and the extracts of Radix Salviae Miltiorrhizae and the others, mix well and make granules. Extract the granules for 3 times with 60% alcohol, 2 hours for the first time, 1 hour for the second and third time each. Filter, then combine the filtrates, recover to non-alcohol. Add water to established amount, mix well, stand, filter, add sodium benzoate to the filtrate, heat to boil, cold, subpackage, sterilize and make oral liquid for use. Usage: take orally, 10 ml each time, 3 times each day.

EXAMPLE 4

Granule

| | |
|---|---|
| Ant | 400 g |
| Radix Salviae Miltiorrhizae | 130 g |
| Radix Aconiti Preparata | 65 g |
| Radix Ginseng | 50 g |
| Caulis Spatholobi | 50 g |
| Ramulus Cinnamomi | 30 g |

In above six crude drugs, pulverize ant, Radix Ginseng and Radix Aconiti Preparata to fine powder, sieve, and mix well; pulverize Radix Salviae Miltiorrhizae and Ramulus Cinnamomi to coarse powder respectively, percolate with 90% alcohol as solvent, pressure reduction concentrate the percolate by recovering alcohol to obtain the extract with relative density of 1.30-1.32 (55° C.). Combine the residues with Caulis Spatholobi and decoct with water, filter, pressure reduction concentrate the filtrates to obtain the extract with relative density of 1.35-1.38 (60° C.), combine the above fine powder and extracts of Radix Salviae Miltiorrhizae and the other crude drugs, mix well, then add proper amount of canesugar and dextrin, mix well, make granules with alcohol, dry and fill in bags for use. Usage: take orally, 3 g each time, 3 times each day.

EXAMPLE 5

Dropping Pill

| | |
|---|---|
| Ant | 400 g |
| Radix Salviae Miltiorrhizae | 130 g |
| Radix Aconiti Preparata | 65 g |
| Radix Ginseng | 50 g |
| Caulis Spatholobi | 50 g |
| Ramulus Cinnamomi | 30 g |
| Cortex Kalopanacis | 50 g |
| Herba speranskiae tuberculatae | 50 g |
| Cortex Phellodendri | 30 g |
| Rhizoma Atractylodis | 45 g |
| Rhizoma Alismatis | 30 g |
| Herba Lycopodii | 30 g |
| Semen Coicis | 50 g |

Pulverize ant, Radix Ginseng and Radix Aconiti Preparata to fine powder, sieve, and mix well; pulverize Radix Salviae Miltiorrhizae, Ramulus Cinnamomi and Rhizoma Atractylodis to coarse powder respectively, percolate with 90% alcohol as solvent, and pressure reduction concentrate the percolate by recovering alcohol to obtain the extract with relative density of 1.30-1.32 (55° C.). Combine the residues with Caulis Spatholobi, Semen Coicis, Cortex Kalopanacis, Herba speranskiae tuberculatae, Cortex Phellodendri, Rhizoma Alismatis, and Herba Lycopodii, decoct with water, filter, pressure reduction concentrate the filtrates to obtain the extract with relative density of 1.35-1.38 (60° C.), combine the above fine powder and extracts of Radix Salviae Miltiorrhizae and the other crude drugs, mix well, make granules. Add the above granules in PEG molten by hexane, stir well, transfer the mixture to the feeding container of a dropping machine, keep the temperature (90° C.) and drop into methyl silicone oil cooled until 5~10° C. at the speed of 30 r/min. After shaping, take out of the dripping pills, and remove the coolant by absorption, and dry for use. Usage: take orally, 10 pills each time, 3 times each day.

EXAMPLE 6

Soft Capsule

| | |
|---|---|
| Ant | 330 g |
| Radix Salviae Miltiorrhizae | 120 g |
| Radix Aconiti Preparata | 60 g |
| Radix Ginseng | 40 g |
| Caulis Spatholobi | 60 g |
| Ramulus Cinnamomi | 40 g |
| Semen Coicis | 60 g |
| Cortex Kalopanacis | 60 g |
| Herba speranskiae tuberculatae | 60 g |
| Cortex Phellodendri | 40 g |
| Rhizoma Atractylodis | 40 g |
| Rhizoma Alismatis | 40 g |
| Herba Lycopodii | 40 g |

Pulverize ant, Radix Ginseng and Radix Aconiti Preparata to fine powder, sieve, and mix well; pulverize Radix Salviae Miltiorrhizae, Ramulus Cinnamomi and Rhizoma Atractylodis to coarse powder respectively, percolate with 90% alcohol as solvent, and pressure reduction concentrate the percolate by recovering alcohol to obtain the extract with relative density of 1.30-1.32 (55° C.). Combine the residues with Caulis Spatholobi, Semen Coicis, Cortex Kalopanacis, Herba speranskiae tuberculatae, Cortex Phellodendri, Rhizoma Alismatis, and Herba Lycopodii, then decoct with water, combine all the decoction, filter, pressure reduction concentrate the filtrates to obtain the extract with relative density of 1.35-1.38 (60° C.), combine the above fine powder and extracts of Radix Salviae Miltiorrhizae and the other crude drugs, mix well, make granules. Take two thirds of the above granules and add 55% alcohol, stir well, stand for 30 hours to obtain the supernatant, recover alcohol from supernatant, concentrate and dry, mix with residue third of the granules, crush to impalpable powder, add proper amount of beeswax and vegetable oil, stir well, make suspension, then compress into soft capsules for use. Usage: take orally, 4 capsules each time, 3 times each day.

EXAMPLE 7

Dropping Pill

| | |
|---|---|
| Ant | 330 g |
| Radix Salviae Miltiorrhizae | 120 g |
| Radix Aconiti Preparata | 60 g |
| Radix Ginseng | 40 g |
| Caulis Spatholobi | 60 g |
| Ramulus Cinnamomi | 40 g |
| Semen Coicis | 60 g |
| Cortex Kalopanacis | 60 g |
| Herba speranskiae tuberculatae | 60 g |
| Cortex Phellodendri | 40 g |
| Rhizoma Atractylodis | 40 g |
| Rhizoma Alismatis | 40 g |
| Herba Lycopodii | 40 g |

-continued

| | |
|---|---|
| Scolopendra | 5 g |
| Zaocys | 5 g |

Pulverize ant, Radix Ginseng, Radix Aconiti Preparata, Scolopendra, and Zaocys to fine powder, sieve, and mix well; pulverize Radix Salviae Miltiorrhizae, Ramulus Cinnamomi and Rhizoma Atractylodis to coarse powder respectively, percolate with 90% alcohol as solvent, and pressure reduction concentrate the percolate by recovering alcohol to obtain the extract with relative density of 1.30-1.32 (55° C.). Combine the residues with Caulis Spatholobi, Semen Coicis, Cortex Kalopanacis, Herba speranskiae tuberculatae, Cortex Phellodendri, Rhizoma Alismatis, and Herba Lycopodii, then decoct with water for two times, 1.5 hours each time, combine all the decoction, filter, pressure reduction concentrate the filtrates to obtain the extract with relative density of 1.35-1.38 (60° C.), combine the above fine powder and each of extracts, mix well, make granules. Add the above granules in PEG molten by hexane, stir well, transfer the mixture to the feeding container of a dropping machine, keep the temperature (90° C.) and drop into methyl silicone oil cooled until 5~10° C. at the speed of 30 r/min. After shaping, take out of the dripping pills, and remove the coolant by absorption, and dry for use.

The invention claimed is:

1. A composition wherein the composition comprises extracts having the following weight ratios:

| | |
|---|---|
| Ant extract | 280-500 parts; |
| Radix Salviae Miltiorrhizae extract | 100-200 parts; |
| Radix Aconiti Preparata extract | 35-100 parts; |
| Radix Ginseng extract | 20-80 parts; |
| Caulis Spatholobi extract | 30-75 parts; |
| Ramulus Cinnamomi extract | 25-80 parts; |
| Cortex Kalopanacis extract | 25-70 parts; |
| Herba speranskiae tuberculatae extract | 25-70 parts; |
| Cortex Phellodendri extract | 25-70 parts; |
| Rhizoma Atractylodis extract | 25-70 parts; |
| Rhizoma Alismatis extract | 25-70 parts; |
| Herba Lycopodii extract and | 25-70 parts; |
| Semen Coicis | 35-70. |

2. A composition according to claim 1, wherein the composition comprises extracts having the following weight ratios:

| | |
|---|---|
| Ant extract | 300-400 parts; |
| Radix Salviae Miltiorrhizae extract | 120-150 parts; |
| Radix Aconiti Preparata extract | 40-70 parts; |
| Radix Ginseng extract | 30-50 parts; |
| Caulis Spatholobi extract | 40-60 parts; |
| Ramulus Cinnamomi extract | 35-50 parts; |
| Cortex Kalopanacis extract | 35-50 parts; |
| Herba speranskiae tuberculatae extract | 35-50 parts; |
| Cortex Phellodendri extract | 35-50 parts; |
| Rhizoma Atractylodis extract | 35-50 parts; |
| Rhizoma Alismatis extract | 35-50 parts; |
| Herba Lycopodii extract and | 35-50 parts; |
| Semen Coicis extract | 45-70 parts. |

3. A composition according to claim 1, wherein the composition comprises extracts having the following weight ratios:

| | |
|---|---|
| Ant extract | 280-500 parts; |
| Radix Salviae Miltiorrhizae extract | 100-150 parts; |
| Radix Aconiti Preparata extract | 35-70 parts; |
| Radix Ginseng extract | 20-50 parts; |
| Caulis Spatholobi extract | 30-75 parts; |
| Ramulus Cinnamomi extract | 25-50 parts; |
| Cortex Kalopanacis extract | 25-70 parts; |
| Herba speranskiae tuberculatae extract | 25-70 parts; |
| Cortex Phellodendri extract | 25-50 parts; |
| Rhizoma Atractylodis extract | 25-50 parts; |
| Rhizoma Alismatis extract | 25-50 parts; |
| Herba Lycopodii extract | 25-50 parts; |
| Semen Coicis extract | 35-70 parts; |
| Scolopendra extract and | 4-10 parts; |
| Zaocys extract | 4-10 parts. |

4. A composition according to claim 3, wherein the composition comprises extracts having the following weight ratios:

| | |
|---|---|
| Ant extract | 300-400 parts; |
| Radix Salviae Miltiorrhizae extract | 120-140 parts; |
| Radix Aconiti Preparata extract | 45-60 parts; |
| Radix Ginseng extract | 20-50 parts; |
| Caulis Spatholobi extract | 45-60 parts; |
| Ramulus Cinnamomi extract | 25-40 parts; |
| Cortex Kalopanacis extract | 35-60 parts; |
| Herba speranskiae tuberculatae extract | 35-60 parts; |
| Cortex Phellodendri extract | 25-40 parts; |
| Rhizoma Atractylodis extract | 25-40 parts; |
| Rhizoma Alismatis extract | 25-40 parts; |
| Herba Lycopodii extract | 25-40 parts; |
| Semen Coicis extract | 45-60 parts; |
| Scolopendra extract | 4-10 parts; |
| Zaocys extract | 4-10 parts. |

5. A composition according to claim 4, wherein the composition comprises extracts having the following weight ratios:

| | |
|---|---|
| Ant extract | 330 parts; |
| Radix Salviae Miltiorrhizae extract | 120 parts; |
| Radix Aconiti Preparata extract | 60 parts; |
| Radix Ginseng extract | 40 parts; |
| Caulis Spatholobi extract | 60 parts; |
| Ramulus Cinnamomi extract | 40 parts; |
| Cortex Kalopanacis | 60 parts; |
| Herba speranskiae tuberculatae extract | 60 parts; |
| Cortex Phellodendri extract | 40 parts; |
| Rhizoma Atractylodis extract | 40 parts; |
| Rhizoma Alismatis extract | 40 parts; |
| Herba Lycopodii extract | 40 parts; |
| Semen Coicis extract | 60 parts; |
| Scolopendra extract and | 5 parts; |
| Zaocys extract | 5 parts. |

6. A composition according to claim 3, wherein the composition is in a dosage form selected from the group consisting of tablets, capsules, pills, granules, suspensions, and liquids.

7. A composition according to claim 6, wherein the capsules are prepared by the following method: pulverizing the ant extract, Radix Ginseng extract, Radix Aconiti Preparata extract, Scolopendra extract, and Zaocys extract, into a fine powder, and sieving, and mixing well, and then pulverizing the Radix Salviae Miltiorrhizae extract, Ramulus Cinnamomi extract, and Rhizoma Atractylodis extract, into a coarse powder, and then perculating with 70-90% alcohol as the solvent, to form a perculate, pressure reducing the perculate into a concentrate by recovering the alcohol to obtain an extract having a relative density of 1.30-1.32 at 55° C., combining the extracts with Caulis Spatholobi extract, Semen Colds extract, Cortex Kalopanacis extract, Herba speranskiae tuberculatae extract, Cortex Phellodendri extract, Rhizoma Alismatis extract, and Herba Lycopodil extract, then decocting with water twice, 1.5 hours each time, combining all of the extracts, filtering, further pressure reducing the extracts to obtain an extract with a relative density of 1.35-1.38 at 60° C., combining the extracts, mixing well, making granules, drying, crushing, sieving, and filling the extracts into capsules for use.

8. A composition according to claim 6, wherein the pills are prepared by the following method: pulverizing the ant extract, Radix Ginseng extract, Radix Aconiti Preparata extract, Scolopendra extract, and Zaocys extract, into a fine powder, and sieving, and mixing well, and then pulverizing the Radix Salviae Miltiorrhizae extract, Ramulus Cinnamomi extract, and Rhizoma Atractylodis extract, into a coarse powder, and then perculating with 70-90% alcohol as the solvent, to form a perculate, pressure reducing the perculate into a concentrate by recovering the alcohol to obtain an extract having a relative density of 1.30-1.32 at 5500, combining the extracts with Caulis Spatholobi extract, Semen Coicis extract, Cortex Kalopanacis extract, Herba speranskiae tuberculatae extract, Cortex Phellodendri extract, Rhizoma Alismatis extract, and Herba Lycopodii extract, then decocting with water twice, 1.5 hours each time, combining all of the extracts, filtering, further pressure reducing the extracts to obtain an extract with a relative density of 1.35-1.38 at 60° C., combining the extracts, mixing well, making granules, adding the granules to a molten form with hexane, stirring well, transferring the mixture to a feeding container in a machine, maintaining the temperature at 90° C. and then dropping the mixture into methyl silicone oil, cooling until the temperature reaches 5-10° C. at a machine speed of 30 r/min, taking out the pills and removing the coolant by absorption, and drying the pills for use.

9. A composition according to claim 4, wherein the composition is in a dosage form selected from the group consisting of tablets, capsules, pills, granules, suspensions, and liquids.

10. A composition according to claim 5, wherein the composition is in a dosage form selected from the group consisting of tablets, capsules, pills, granules, suspensions, and liquids.

11. A composition according to claim 9, wherein the capsules are prepared by the following method: pulverizing the ant extract, Radix Ginseng extract, Radix Aconiti Preparata extract, Scolopendra extract, and Zaocys extract, into a fine powder, and sieving, and mixing well, and then pulverizing the Radix Salviae Miltiorrhizae extract, Ramulus Cinnamomi extract, and Rhizoma Atractylodis extract, into a coarse powder, and then perculating with 70-90% alcohol as the solvent, to form a perculate, pressure reducing the perculate into a concentrate by recovering the alcohol to obtain an extract having a relative density of 1.30-1.32 at 55° C., combining the extracts with Caulis Spatholobi extract, Semen Coicis extract, Cortex Kalopanacis extract, Herba speranskiae tuberculatae extract, Cortex Phellodendri extract, Rhizoma Alismatis extract, and Herba Lycopodii extract, then decocting with water twice, 1.5 hours each time, combining all of the extracts, filtering, further pressure reducing the extracts to obtain an extract with a relative density of 1.35-1.38 at 60° C., combining the extracts, mixing well, making granules, drying, crushing, sieving, and filling the extracts into capsules for use.

12. A composition according to claim 10, wherein the capsules are prepared by the following method: pulverizing the ant extract, Radix Ginseng extract, Radix Aconiti Preparata extract, Scolopendra extract, and Zaocys extract, into a fine powder, and sieving, and mixing well, and then pulverizing the Radix Salviae Miltiorrhizae extract, Ramulus Cinnamomi extract, and Rhizoma Atractylodis extract, into a coarse powder, and then perculating with 70-90% alcohol as the solvent, to form a perculate, pressure reducing the perculate into a concentrate by recovering the alcohol to obtain an extract having a relative density of 1.30-1.32 at 55° C., combining the extracts with Caulis Spatholobi extract, Semen Colds extract, Cortex Kalopanacis extract, Herba speranskiae tuberculatae extract, Cortex Phellodendri extract, Rhizoma Alismatis extract, and Herba Lycopodil extract, then decocting with water twice, 1.5 hours each time, combining all of the extracts, filtering, further pressure reducing the extracts to obtain an extract with a relative density of 1.35-1.38 at 60° C., combining the extracts, mixing well, making granules, drying, crushing, sieving, and filling the extracts into capsules for use.

13. A composition according to claim 9, wherein the pills are prepared by the following method: pulverizing the ant extract, Radix Ginseng extract, Radix Aconiti Preparata extract, Scolopendra extract, and Zaocys extract, into a fine powder, and sieving, and mixing well, and then pulverizing the Radix Salviae Miltiorrhizae extract, Ramulus Cinnamomi extract, and Rhizoma Atractylodis extract, into a coarse powder, and then perculating with 70-90% alcohol as the solvent, to form a perculate, pressure reducing the perculate into a concentrate by recovering the alcohol to obtain an extract having a relative density of 1.30-1.32 at 55° C., combining the extracts with Caulis Spatholobi extract, Semen Coicis extract, Cortex Kalopanacis extract, Herba speranskiae tuberculatae extract, Cortex Phellodendri extract, Rhizoma Alismatis extract, and Herba Lycopodii extract, then decocting with water twice, 1.5 hours each time, combining all of the extracts, filtering, further pressure reducing the extracts to obtain an extract with a relative density of 1.35-1.38 at 60° C., combining the extracts, mixing well, making granules, adding the granules to a molten form with hexane, stirring well, transferring the mixture to a feeding container in a machine, maintaining the temperature at 90° C. and then dropping the mixture into methyl silicone oil, cooling until the temperature reaches 5-10° C. at a machine speed of 30 r/min, taking out the pills and removing the coolant by absorption, and drying the pills for use.

14. A composition according to claim 10, wherein the pills are prepared by the following method: pulverizing the ant extract, Radix Ginseng extract, Radix Aconiti Preparata extract, Scolopendra extract, and Zaocys extract, into a fine powder, and sieving, and mixing well, and then pulverizing the Radix Salviae Miltiorrhizae extract, Ramulus Cinnamomi extract, and Rhizoma Atractylodis extract, into a coarse powder, and then perculating with 70-90% alcohol as the solvent, to form a perculate, pressure reducing the perculate into a concentrate by recovering the alcohol to obtain an extract having a relative density of 1.30-1.32 at 55° C., combining the extracts with Caulis Spatholobi extract, Semen Coicis extract, Cortex Kalopanacis extract, Herba speranskiae tuberculatae extract, Cortex Phellodendri extract, Rhizoma Alismatis extract, and Herba Lycopodii extract, then decocting with water twice, 1.5 hours each time, combining all of the extracts, filtering, further pressure reducing the extracts to obtain an extract with a relative density of 1.35-1.38 at 60° C., combining the extracts, mixing well, making granules, adding the granules to a molten form with hexane, stirring well, transferring the mixture to a feeding container in a machine, maintaining the temperature at 90° C. and then dropping the mixture into methyl silicone oil, cooling until the temperature reaches 5-10° C. at a machine speed of 30 r/min, taking out the pills and removing the coolant by absorption, and drying the pills for use.

\* \* \* \* \*